United States Patent [19]

Kobayashi

[11] Patent Number: 4,900,144
[45] Date of Patent: Feb. 13, 1990

[54] THREE-DIMENSIONAL SHAPE MEASUREMENT APPARATUS

[75] Inventor: Koji Kobayashi, Hino, Japan
[73] Assignee: Kowa Company Ltd., Japan
[21] Appl. No.: 262,525
[22] Filed: Oct. 25, 1988
[30] Foreign Application Priority Data Oct. 28, 1987 [JP] Japan .................................. 62-270442

[51] Int. Cl.4 .......................... A61B 3/14; G01B 11/24
[52] U.S. Cl. .................................... 351/206; 250/560; 356/376
[58] Field of Search ................ 250/560; 351/206, 208, 351/211; 354/62; 356/376

[56] References Cited

U.S. PATENT DOCUMENTS

| | | | |
|---|---|---|---|
| 4,213,678 | 7/1980 | Pomerantzeff et al. | 351/206 |
| 4,423,931 | 1/1984 | Shapiro | 356/376 |
| 4,715,703 | 12/1987 | Cornsweet et al. | 351/206 |

Primary Examiner—Edward P. Westin
Attorney, Agent, or Firm—Bruce L. Adams; Van C. Wilks

[57] ABSTRACT

A three-dimensional shape measurement apparatus uses a laser beam to illuminate an object. The light reflected from the object is processed to obtain information about the shape of the object in three dimensions. As the beam moves over contour features of the object, there is a corresponding displacement of the focal point of the light reflected back from the object which is calculated to convert it to depth-wise shape information. The apparatus includes a laser light source; deflectors for scanning the laser beam at a set frequency; an optical system for projecting the laser beam scanned by the optical deflectors at the object; detection slits arranged parallel to the direction in which the reflected light is scanned and facing the object along on an optical axis that is perpendicular to the direction of the scanning by the optical deflectors, the slits being placed a certain distance from a point that is optionally conjugate with the object; photosensors for detecting light passing through the detection slits; and a signal processor to eliminate the effect of the reflection characteristics of the object.

32 Claims, 4 Drawing Sheets

THREE-DIMENSIONAL SHAPE MEASUREMENT APPARATUS

BACKGROUND OF THE INVENTION

1. Field of the Invention

This invention relates to a three-dimensional shape measurement apparatus which directs a laser beam at an object, picks up the light reflected back from the object, photoelectrically converts the light and subjects it to signal processing to obtain three-dimensional information about the object.

2. Description of the Prior Art

There are many non-contact, optical methods of measuring the three-dimensional shape or profile of an object ( See, for example, Applied Optics, Vol.21(1982) page 3200, Vol. 23(1984) page 3837 or Vol. 25(1986) page 1630). One medical application of an optical three-dimensional measuring method that has been attracting attention recently is an apparatus for obtaining three-dimensional information about the human eye fundus.

As well as its use in ophthalmology, examination of the eye fundus is also employed in internal medicine for diagnosing hypertension, diabetes, diseases of the cerebral nerves and other such disorders. For this, one method in widespread use is that of using a fundus camera to conduct a photographic examination. However, because quantitative measurement, particularly of the degree of depression of the optic papilla of the eye fundus is useful in the early detection of glaucoma, and as such is directly related to the prevention of loss of vision, recently there have also been attempts to acquire three-dimensional information about the fundus, in addition to the two-dimensional information provided by the usual fundus camera.

One such three-dimensional fundus measuring method consists of projecting a fixed stripe or grid pattern on the fundus and observing it at a prescribed angle from a separate direction in order to measure the deviation of the stripe or grid image from a straight line. The principle of triangulation is then used to convert the amount of deviation in the depth direction and thereby quantitatively evaluate the state of fundus depression (see, for example, U.S. Pat. No. 4,423,931).

In another method, based on the principle of stereoscopic photography, a fundus camera or the like is used to take two photographs of the fundus at different angles of pupil incidence. By then analyzing the images of the two fundus photographs, depth information can be extracted and quantified. Apparatuses have also been developed in which the photographic film of the fundus camera is replaced by two equivalent television cameras positioned at different observation angles and linked to a computer so as to provide three-dimensional information automatically (see, for example, U.S. Pat. No. 4,715,703).

However, with each of these methods still suffering from low spatial resolution capabilities and difficulties relating to accuracy and the degree of reproducibility, their clinical feasibility remains uncertain. One reason for this relates to physical restrictions inherent in the fundus of the human eye; i.e., observation of the inner surface of a relatively large spherical object via the limited window of a small pupil. In the case of both triangulation and stereophotography, it is not possible to increase the angular difference of the observations. Another reason is the very low reflectivity and contrast of the fundus, which is a product of reflection characteristics specific to the object, i.e., the abrupt changes in the reflection intensity of the optic papilla of the eye fundus. It is mainly for these two reasons that, in the case of measuring three-dimensional shapes, it is difficult to improve spatial resolution capabilities, accuracy and reproducibility.

Another problem with methods of measurement using the conventional apparatuses is that none of them are methods of directly measuring depth information, and as such, in each case processing time is required. The method employing the principle of triangulation requires time for the calculations involved in the conversion of the amount of stripe or grid image deviation to depth information, and the stereophotographic-based method requires time for analyzing the image information in the two photographs to elucidate depth information. Also, there is a tradeoff between shortening of the processing time and improvement in the spatial resolution. Computer advances can reduce the time needed for the processing, but not enough for clinical applications.

One electronic ophthalmic examination apparatus for human eye fundus applications that employs laser scanning was developed by the Retina Foundation of the U.S.(See U.S. Pat. No. 4,213,678 and Japanese Laid-open Patent Publication 62-117524.) This apparatus has attracted attention for the many features it possesses, such as the ability to display in real-time on a monitor television a high-contrast video image of the eye fundus, using a low level of illumination. In a paper (Applied Optics, vol. 19 (1980) page 2991), the Retina Foundation mentioned that it was feasible to use this laser-beam scanning method to ascertain the three-dimensional configuration of the eye fundus. However, the method is based on the same principle of stereoscopic photography explained above, in which different angles of pupil incidence are used, so there are problems concerning resolution and accuracy. As such, regarding the direct determination of the three-dimensional shape of the fundus, the method is not practicable.

SUMMARY OF THE INVENTION

An object of the present invention is therefore to provide a new type of practical, three-dimensional shape measurement apparatus that can be applied to objects, such as the fundus of the human eye, where it is impossible to obtain a large angular difference such as is needed for triangulation-based observations, and which exhibit abrupt changes in reflection intensity.

To attain this object, the present invention comprises a three-dimensional shape measurement apparatus which directs a laser beam at an object, detects the light reflected back from the object, photoelectrically converts the light and subjects it to signal processing to obtain three-dimensional information about the object, comprising: a laser light source that generates a laser beam; a first optical deflector for scanning the laser beam in one direction at a predetermined frequency; a second optical deflector for scanning the laser beam in a direction that is perpendicular to the above said direction at a predetermined frequency; an optical system for projecting the laser beam scanned two-dimensionally by the first and second optical deflectors at the object; optical means for scanning light reflected from the object and guiding it so that scanning is stationary fixed at least with respect to the direction of scanning by the second optical deflector; detection means for acquiring information relating to the shape characteristics of the object in a direction of an optical axis that is perpendicular to the direction of the scanning by the first and second optical deflectors, depending on displacement of the focal point of the light reflected from the object; and signal processing means for removing from the output signal of the detection means the influence of the optical reflection characteristics of the object.

The three-dimensional shape measurement apparatus of this invention whereby a laser beam is directed at an object, the light reflected back from the object is picked up, photoelectrically converted and subjected to signal processing to obtain three-dimensional information about the object also comprises: a laser light source that generates a laser beam; an optical deflector for scanning the laser beam at a predetermined frequency; an optical system for projecting the laser beam scanned by the optical deflector at the object; two detection slits oriented in a direction parallel to the direction in which light reflected from the object is scanned and facing the object along an optical axis that is perpendicular to the direction of the scanning by the optical deflector, said detection slits being mutually displaced by a prescribed distance in the vicinity of a position that is optically conjugate with the object; two photosensors for detecting light passing through the respective detection slits; and signal processing means for cancelling out from the output signal of the photosensors optical reflection characteristic information of the object for acquiring information relating to the shape characteristics of the object in a direction of an optical axis toward the object that is perpendicular to the direction of scanning by the optical deflector.

The three-dimensional shape measurement apparatus which directs a laser beam at an object, detects the light reflected back from the object, photoelectrically converts the light and subjects it to signal processing to obtain three-dimensional information about the object further comprises: a laser light source that generates a laser beam; an optical system for projecting the laser beam from the laser light source at the object; two detection apertures mutually displaced by a prescribed distance in the vicinity of a position that is optically conjugate with the object; two photosensors for detecting light reflected from the object passing through the respective detection apertures; a divider circuit for dividing the output of one photosensor by that of the other; and a correction means for correcting prescribed non-linearity in the output of the divider.

With this arrangement in which the light reflected from the object is scanned and an optical means is used for guidance purposes to fix the scanning, on the detection side the scanning of the reflected light is fixed at least in one dimension, enabling information to be detected in the direction of the optical axis, by using a detection slit, for example, at the focal point position. This enables it to be applied to objects such as the fundus of the human eye, where it is impossible to obtain a large angular difference such as is needed for observations for triangulation. As the apparatus also has a means that uses a divider to cancel out optical reflection characteristic information of the object, even when the object exhibit abrupt changes in reflectivity, the effect is nullified, so the accuracy and reproducibility are high. Further, using optical deflectors as the scanning means makes it possible to achieve high spatial resolution in the measurements by employing many measuring points. And, as information in the direction of the optical axis is detected directly, the time needed for processing the measurements can be made relatively short.

DETAILED DESCRIPTION OF THE PREFERRED EMBODIMENTS

The embodiments of the present invention will now be described in the following with reference to FIGS. 1 to 5.

Figure 1:
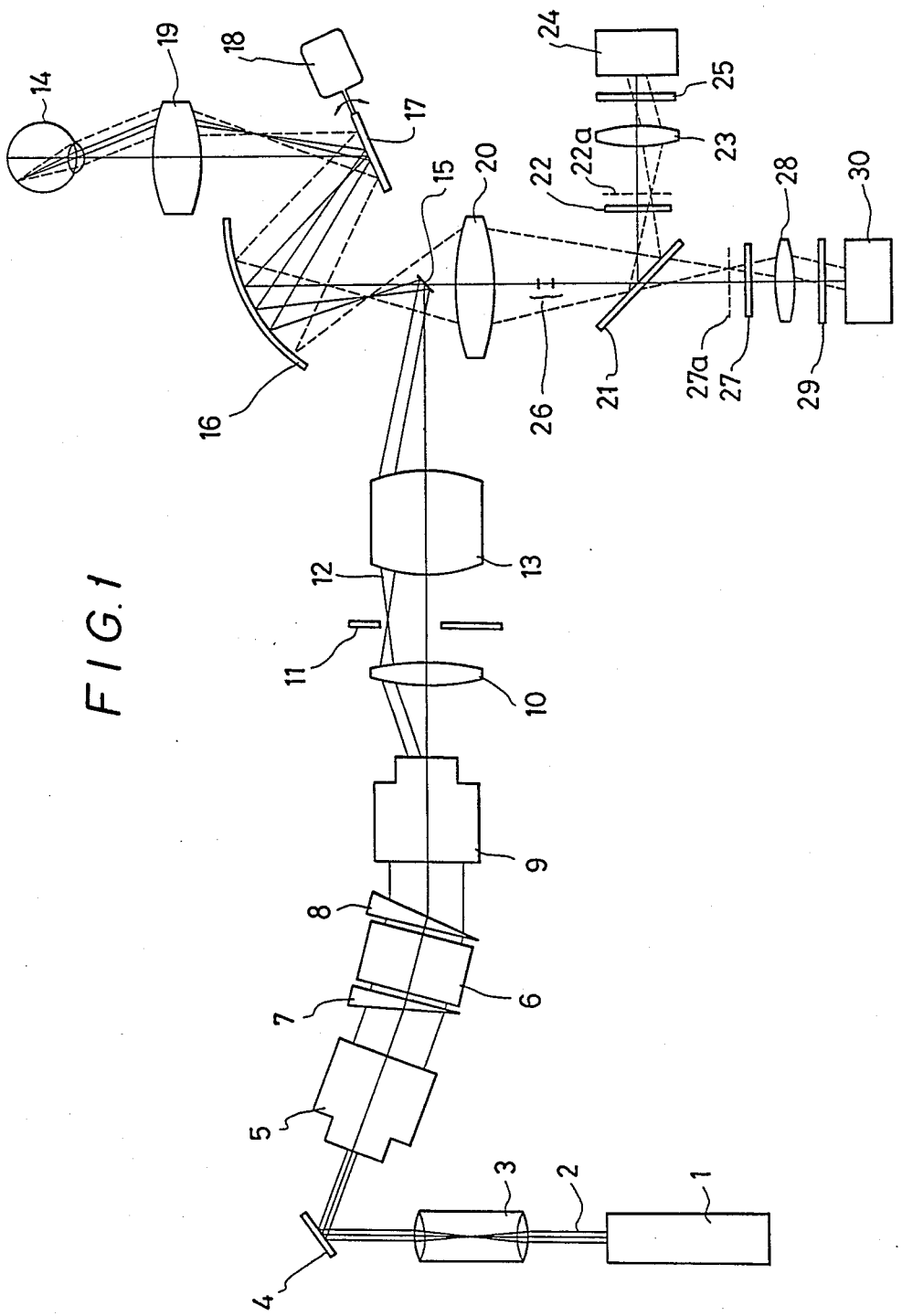
FIG. 1 is a schematic illustration of the overall configuration of the optical system of the apparatus according to the present invention.

FIG. 1 is a general schematic of the optical system arrangement of the three-dimensional shape measurement apparatus according to the present invention. In FIG. 1, reference numeral 1 denotes a laser light source of helium-neon (He-Ne) or argon ($Ar^+$), for example. A laser beam 2 produced by the laser light source 1 is expanded to a specific size by a beam expander 3 and is then reflected by a mirror 4 to impinge on a lens 5. The lens 5 is for shaping the laser beam for the rectangular aperture of a following acousto-optical deflector (AOD) 6, and incorporates a multiplicity of cylindrical lenses. The AOD 6 is bracketed by a pair of prisms 7 and 8 which compensate for the wavelength dependency of the angle of incidence and angle of emergence of the laser beam with respect to the AOD 6. The laser beam deflected in one dimension (horizontally) by the AOD 6 is reformed from the rectangular (elliptical) shape to its original circular shape by a lens 9 which is constituted analogously to the lens 5, following which the beam passes through a lens 10 and a slit 11. The slit 11 is for blocking zero-order light (not shown) from the AOD 6 so as to utilize only first-order diffraction light. First-order diffraction light 12 from the slit 11 is scanned one-dimensionally with the central portion of a mirror 15 disposed at a position optically conjugate with the pupil of the eye 14 being examined as the pivot point of deflection.

A laser beam scanning frequency of 15.75 KHz corresponding to the ordinary NTSC standard television horizontal scan rate is selected for the AOD 6. The prisms 7 and 8 may not be required if only a laser beam of one wavelength is used.

The laser beam reflected by the mirror 15 is reflected onto a mirror 17 by a concave mirror 16 which possesses the function of a lens. The mirror 17 is attached to a galvanometer 18 for vertical scanning of the laser beam, and is referred to as an oscillating mirror or a galvanometer mirror. The laser beam scanned two-dimensionally by the mirror 17 is passed through an objective lens 19 and is thereby projected onto the eye fundus via the central portion of the pupil of the eye 14 being examined. The light reflected from the fundus, which in FIG. 1 is indicated by a dashed line, is guided via the objective lens 19 to be reflected again by the mirror 17 and the concave mirror 16. The light reflected from the eye fundus is in a two-dimensionally scanned state, but after being directed onto the concave mirror 16 by the mirror 17 it is fixed in a vertical scanning state by the deflective action of the mirror 17; i.e., it becomes reflected light that is scanned only one-dimensionally.

A vertical scanning frequency of 60 Hz corresponding to the ordinary television vertical scanning frequency is selected for the oscillating mirror 17.

Light reflected from the eye fundus and then reflected by the concave mirror 16 passes around the periphery of the mirror 15, which is the point at which it is separated from the projected laser light. This one-dimensionally scanned reflected light from the fundus that passes around the periphery of the mirror 15 passes through a lens 20. Half of this reflected light is then reflected by a half mirror 21, passes through a detection slit 22 and a lens 23 and is detected by a photosensor 24. Disposed in front of the photosensor 24 is a filter 25 which corresponds to the wavelength of the laser beam. Also, between the lens 20 and the half mirror 21 is a black spot 26 for eliminating the effect of light reflecting from the surface of the objective lens 19.

The other half of the light reflected from the eye fundus is transmitted by the half mirror 21 and, similarly to the reflected half, passes through a detection slit 27, a lens 28 and a filter 29 to a photosensor 30. The filter 29 has the same characteristics as the filter 25, corresponding to the wavelength of the laser beam. As is apparent from FIG. 1, each of the detection slits 22 and 27 has been situated slightly away from the respective positions 22a and 27a that are optical conjugates of the fundus of the eye 14. In addition, viewed along the optical axis in the direction of the eye 14, one of the detection slits is situated slightly to the front, and the other slightly to the rear, of the positions that are the optical conjugates of the fundus of the eye 14.

Figure 2:
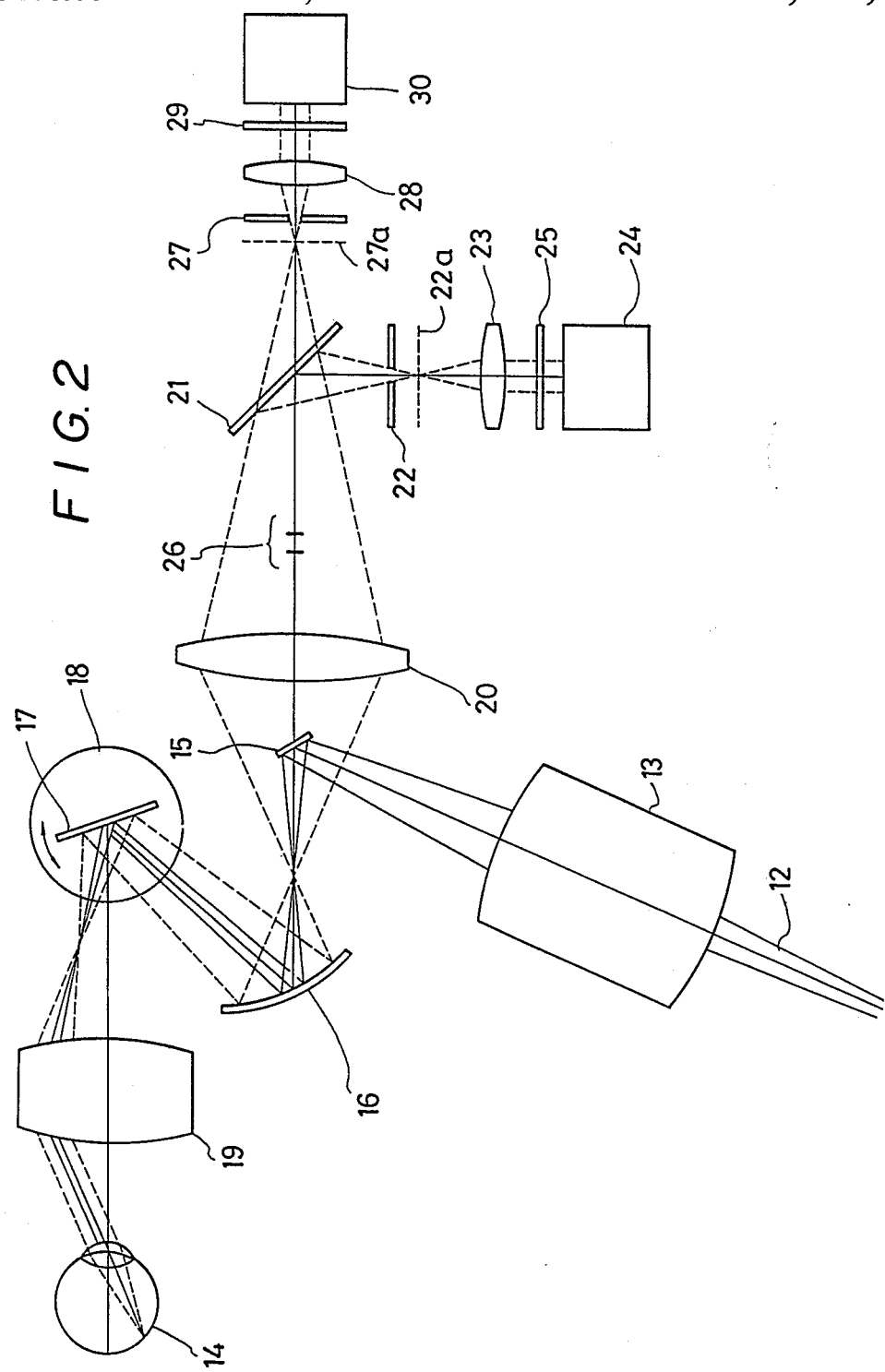
FIG. 2 shows in detail part of the optical system shown in FIG. 1.

FIG. 2 illustrates part of the optical system of FIG. 1, particularly the portion for guiding the light reflected from the fundus, in a configuration that is closer to an actual arrangement. In FIG. 2, the laser beam 12 (first-order diffraction light) deflected one-dimensionally (in the horizontal direction) by the AOD 6 is guided via the lens 13 to be scanned with the mirror 15 as the pivot point of deflection, said mirror 15 being disposed at a position that is optically conjugate with the pupil of the eye being examined.

In FIG. 2 the scanning direction of the first-order diffraction light 12 is perpendicular to the drawing sheet, so the laser beam is therefore depicted as following the central axis of the optical system. The laser beam reflected by the mirror 15 and scanned in the horizontal direction (vertically with reference to the FIG. 2 drawing sheet) is reflected by the concave mirror 16, is again reflected by the oscillating mirror 17 attached to the galvanometer 18 and is also scanned vertically (horizontally with respect to the drawing sheet). The laser beam scanned two-dimensionally (horizontally and vertically) by the oscillating mirror 17 is projected onto the fundus of the eye 14 by the objective lens 19, and the light reflected from the eye fundus, depicted by a dashed line in FIG. 2, is returned through the same optical system elements 19, 17 and 16 as the incident beam.

The light reflected from the eye fundus that has been separated from the incident beam at the mirror 15 passes through the lens 20 and impinges on the half mirror 21 which splits the optical path by reflecting one half of the light and transmitting the other half. The light reflected by the mirror 21 passes through the detection slit 22, lens 23 and filter 25 and is detected by the photosensor 24. The portion of the light transmitted by the mirror 21 passes through the detection slit 27, lens 28 and filter 29 and is detected by the photosensor 30. In FIG. 2, the reflected light from the eye fundus, represented by the dashed lines from the oscillating mirror 17 to the photosensors 24 and 30, is only being scanned horizontally (vertically with reference to the FIG. 2 drawing sheet). This being the case, the laser beam is depicted as following the central axis of the optical system as if it is not being scanned.

As is apparent from the drawing, the two detection slits are oriented so that the reflected light is scanned in a direction that is parallel to the slits, and in a direction that is perpendicular to the slits the scanning is stationary, in addition to which they are oriented along the optical axis toward the eye so that one is displaced slightly to the front, and the other slightly to the rear, of the positions 27a and 22a that are the optical conjugates of the fundus.

The electrical signal obtained as a result of detection and optoelectronic conversion by the photosensors 24 and 30 reflects the reflection characteristics of the fundus of the eye 14. Also, as the frequencies of the horizontal and vertical scanning of the laser beam by the AOD 6 and the oscillating mirror 17 correspond to the scanning rates of an ordinary television, by appropriately amplifying the output signals from the photosensors 24 and 30 for feeding to a television monitor, two-dimensional images of the fundus can be displayed on the screen. The image shown on the monitor will mirror the optical reflection characteristics of the layer of fundus tissue corresponding to the wavelength of the laser beam.

However, because in this case the detection slits 22 and 27 are slightly displaced from the position that is optically conjugate with the fundus, the output signals from the two photosensors that detect the reflected light from the fundus that passes through the two detection slits will differ in intensity depending on the state of the optical conjugate relations between the detection slits and the fundus. That is, assuming the two slits are equal, when the positions that are optically conjugate with the fundus, i.e., the positions of the focal points of the fundus, are an equal distance from the detection slits 22 and 27 the output signals from the two photosensors will be about equal in intensity. However, unevenness in the fundus will cause a slight displacement in the said conjugate positions, giving rise to a difference in intensity between the signals output by the two photosensors.

Figure 3:
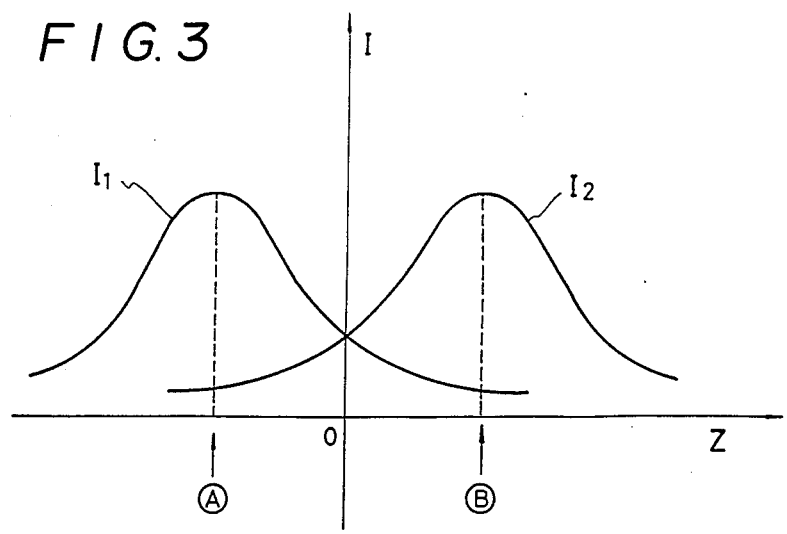
FIG. 3 is a graph showing the characteristic of the output signal of the photosensor of FIG. 2.

FIG. 3 shows a typical characteristic waveform of the signal output by the two photosensors 24 and 30. The horizontal axis represents a distance in the direction along an optical axis Z perpendicular to both the horizontal x and vertical y directions in which the laser beam is scanned, and the vertical axis represents the intensity I of the photosensor output signals. The two waveforms $I_1$, $I_2$ show the changes in the respective output signals of the photosensors 24 and 30, such as when a depression, for example, in the fundus causes the location of the position of optical conjugate with the fundus to shift along the optical axis Z. As is apparent from FIG. 2, when the position 22a that is an optical conjugate of the fundus coincides with the position of the detection slit 22 (indicated in FIG. 3 by A) the intensity $I_l$ of the output signal of the photosensor 24 is at its peak, and on each side thereof there is a smooth fall-off in signal intensity $I_1$. On the other hand, when the position 27a that is an optical conjugate of the fundus coincides with the position of the detection slit 27 (indicated in FIG. 3 by B) the intensity $I_2$ of the output signal of the photosensor 30 is at its peak, falling off to each side thereof in the same way as $I_1$. What has to be noted here is that the signal intensity is completely dependent on the reflectivity of fundus. This means that when the laser beam is scanning a part of the fundus that exhibits high reflectivity the waveform of FIG. 3 shows a proportional increase in size and, conversely, decreases in size when reflectivity is lower.

Figure 4:
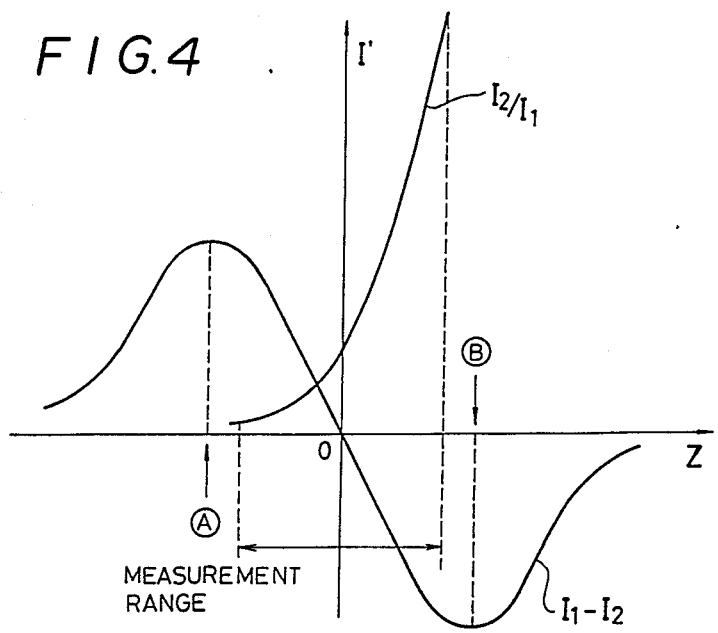
FIG. 4 is a graph showing the characteristic of the computed output signal of the photosensor.

FIG. 4 shows a typical waveform characteristic obtained by computing the output signals of the photosensors 24 and 30 having the type of characteristic shown in FIG. 3. The horizontal axis represents a distance along an optical axis Z and the vertical axis represents the signal intensity $I'$ obtained by computation. The two waveforms were obtained by calculating $I_l - I_2$ and $I_2/I_1$, respectively. The $I_l - I_2$ type of differential characteristic is featured by the intensity value having a zero point and being partially proportional to Z, and because of this it is used in video-disc systems for detection of the position of the focal point in the Z direction.

However, as is clear from the above explanation, because $I_l - I_2$ depends entirely on the reflectivity of the fundus, unless the intensity of the reflected light from the fundus is known, the Z-direction value cannot be determined from the value $I_l - I_2$. Regarding $I_2/I_1$, even if the intensity of $I_l$ and $I_2$ depend on the reflectivity of the fundus, each can cancel out the other by denominator and numerator to make them independent of the fundus reflectivity, and thus making it possible to determine the value in the Z direction from $I_2/I_1$. Expressed mathematically, if $I_0(x, y)$ is the intensity of the reflected light from the fundus, when $$I_1 = f_1(Z) \cdot I_0(x, y)$$

$$I_2 = f_2(Z) \cdot I_0(x, y)$$

as $I_2/I_1 = f_2(Z)/f_1(Z)$, $I_2/I_1$ becomes a prescribed function that depends only on the value of Z, not on the reflectivity, so it is clear that the Z value can be obtained from $I_2/I_1$. As such, by finding the value of $I_2/I_l$ by calculation it is possible to quantify the degree of unevenness three-dimensionally, the amount of displacement in the location of the optically conjugate position along the optical axis Z, i.e., the displacement in the Z direction of each location in the fundus as it is scanned by the laser beam in the x and y directions.

The range of values that can be set along Z, based on such characteristics, becomes a constant measurement range that falls inside the points A and B shown in FIG. 4. Also, as the value of $I_2/I_l$ is not proportional to the Z value but is instead rather non-linear, when it used with an actual measurement apparatus a means of correcting this non-linearity is required.

Moreover, it is, for example, also possible to combine the addition, subtraction, and division to cancel the intensity of the reflected light according to the following equation.

$$(I_1 - I_2)/(I_1 + I_2) = (f_1(Z) - f_2(Z))/(f_1(Z) + f_2(Z))$$

In this case, the calculated value possesses the different non-linearity from that obtained using the value $I_2/I_1$.

Figure 5:
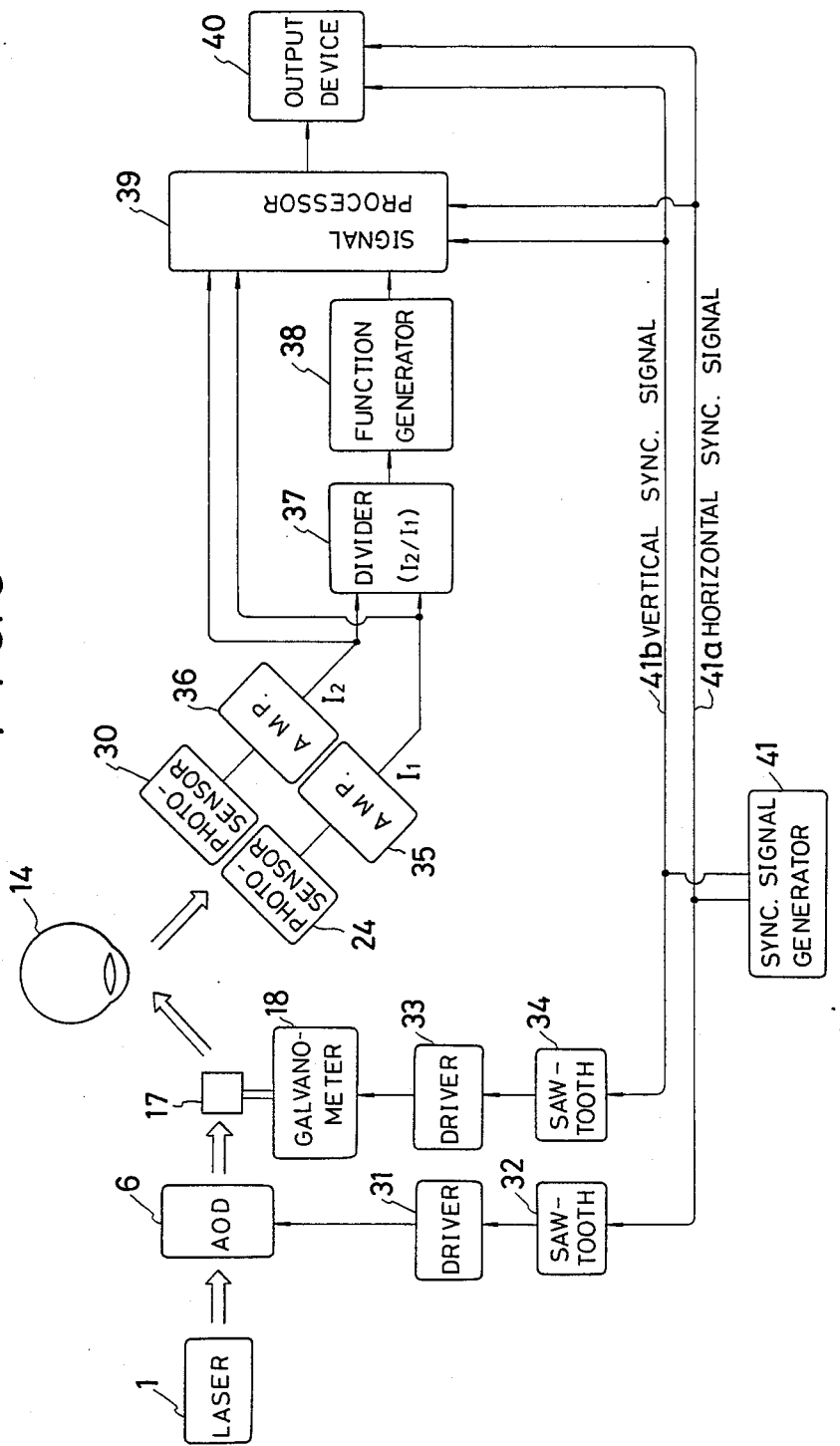
FIG. 5 is a block diagram showing the electrical configuration of the apparatus of the invention.

FIG. 5 is a block diagram illustrating the electrical configuration of the three-dimensional shape measurement apparatus according to the present invention. The laser beam produced by the laser light source 1 is deflected horizontally and vertically by means of the AOD 6 and the oscillating mirror 17, and is beamed at the eye 14 being examined. A driver 31 is connected to the AOD 6, the driver 31 being controlled by a sawtooth signal generated by a sawtooth waveform generator 32. Connected to the galvanometer 18 which drives the mirror 17 is a driver 33 which is controlled by a sawtooth signal generated by a sawtooth waveform generator 34.

The light reflected from the eye 14 is detected by the photosensors 24 and 30, and the output signals therefrom are amplified to the required level by amplifiers 35 and 36. The output signals $I_l$ and $I_2$ from the amplifiers are input to a divider 37, the divisional operation $I_2/I_l$ is performed, and the result is input to a function generator 38. As was explained above, the calculated outputs of photosensors 24 and 30 have the type of intensity characteristics shown in FIG. 4. The purpose of the function generator 38 is to cancel the nonlinearity of the value $I_2/I_l$ seen in FIG. 4. The intensity of the output signal of the function generator is proportional to the displacement of the fundus in the direction of the optical axis Z, i.e., to the degree of unevenness of the fundus. The divider 37 and the function generator 38 may be constituted entirely of analog integrated circuitry, or it may be comprised of A/D, D/A converters and digital operation circuitry.

After the output signals of the function generator 38 and of the amplifiers 35 and 36 are input to a signal processor 39, the information is selected and the prescribed processing carried out, an output device 40 such as a display monitor is used to display the output image. When the signal selected is from the amplifier 35 or 36, the image output is an ordinary two-dimensional depiction of the reflection characteristics of the fundus, while when the function generator 38 signal is selected the image displays unevenness of the fundus surface with different shade levels or colors. Also, microprocessors and software provided in the signal processor 39 can be used to create three-dimensional graphic patterns based on the output signals of the function generator 38, enabling, for example, an observation of the fundus taken at an angle to be displayed on the output device 40 as a three-dimensional bird's-eye view.

The control system of the two-dimensional scanning of the laser beam and the output system that detects and processes the reflected light from the fundus are synchronized by a horizontal synchronizing signal 41a and vertical synchronizing signal 41b from a synchronizing signal generator 41, thereby enabling time-based control of the overall system.

Moreover, although in this embodiment the scanning is fixed(stationary) in the vertical direction at the photosensors, the light reflected from the object (fundus) being scanned by the oscillating mirror only, and two detection slits are therefore used to detect displacement of the focal point of the reflected light, a rotating multi-faced mirror, for example, could of course be used as the horizontal deflector for scanning the reflected light, and when the horizontal scanning is also fixed the detection slit could be replaced by a round aperture. That is, the present invention encompasses use of two deflectors, and the reflected light from the object is scanned with respect to one direction and the scanning is stationary in at least direction. Also encompassed is the arrangement in which the scanning of the reflected light is performed with respect to both directions and the scanning is completely stationary in both directions at the detection aperture, if the arrangement is one that performs detection of information related to shape characteristics of the object in the direction of an optical axis perpendicular to the direction of scanning by the two deflectors, based on the displacement of the focal point of the light reflected from the object.

While the invention has been described with reference to a preferred embodiment in which the object is an eye fundus, it will be understood that the invention is not limited thereto but may be utilized to ascertain three-dimensional shapes such as the features of integrated circuit patterns, or of microorganisms, cells and the like by applying this to, for example, a laser scanning microscope.

As can be seen from the above description, the three-dimensional shape measurement apparatus according to the present invention is new and eminently practical, applicable as it is to objects, such as the fundus of the human eye, which exhibit abrupt changes in reflectivity and where it is impossible to obtain the type of large angular difference needed by the triangulation method. It can also be used to carry out measurements on a television monitor at a resolution as high as the screen resolution; and it has good accuracy and reproducibility. In addition to this, the time required for processing the measurements can be shortened: by using different shades to represent the unevenness in the contours of the object, it is possible to conduct the measurements on a fully real-time basis and at the same time obtain ordinary two-dimensional information relating to the reflection characteristics of an object.

What is claimed is:

1. A three-dimensional shape measurement apparatus which directs a laser beam at an object, detects light reflected back from the object, photoelectrically converts the light and subjects it to signal processing to obtain three-dimensional information about the object, comprising:
   a laser light source that generates a laser beam;
   a first optical deflector for scanning the laser beam in one direction at a predetermined frequency;
   a second optical deflector for scanning the laser beam in a direction that is perpendicular to the above said direction at a predetermined frequency;
   an optical system for projecting the laser beam scanned two-dimensionally by the first and second optical deflectors at the object;
   optical means for scanning light reflected from the object and guiding it so that scanning is stationary at least with respect to the direction of scanning by the second optical deflector;
   detection means for acquiring information relating to the shape characteristics of the object in a direction of an optical axis that is perpendicular to the direction of the scanning by the first and second optical deflectors, depending on displacement of the focal point of the light reflected from the object; and
   signal processing means for removing from the output signal of the detection means the influence of the optical reflection characteristics of the object.

2. The three-dimensional shape measurement apparatus according to claim 1 wherein the first optical deflector is an acousto-optical deflector.

3. The three-dimensional shape measurement apparatus according to claim 1 wherein the second optical deflector is an oscillating mirror.

4. The three-dimensional shape measurement apparatus according to claim 1 wherein the optical means includes the second optical deflector.

5. The three-dimensional shape measurement apparatus according to claim 1 wherein the scanning frequency of the second optical deflector is lower than the scanning frequency of the first optical deflector.

6. The three-dimensional shape measurement apparatus according to claim 1 wherein the detection means includes two detection slits oriented in a direction parallel to the direction in which light reflected from the object is scanned and facing the object along an optical axis that is perpendicular to the direction of the scanning by the optical deflector, said detection slits being mutually displaced by a prescribed distance in the vicinity of a position that is optically conjugate with the object.

7. The three-dimensional shape measurement apparatus according to claim 6 wherein one of the two detection slits is located to the front of the said conjugate position and the other is located to the rear thereof.

8. The three-dimensional shape measurement apparatus according to claim 1 wherein the signal processing means includes a divider circuit and a function generator circuit.

9. A three-dimensional shape measurement apparatus which directs a laser beam at an object, detects light reflected back from the object, photoelectrically converts the light and subjects it to signal processing to obtain three-dimensional information about the object, comprising:
   a laser light source that generates a laser beam;
   an optical deflector for scanning the laser beam at a predetermined frequency;
   an optical system for projecting the laser beam scanned by the optical deflector at the object;
   two detection slits oriented in a direction parallel to the direction in which light reflected from the object is scanned and facing the object along an optical axis that is perpendicular to the direction of scanning by the optical deflector, said detection slits being mutually displaced by a prescribed distance in the vicinity of a position that is optically conjugate with the object;
   two photosensors for detecting light passing through the respective detection slits;
   signal processing means for cancelling out from the output signal of the photosensors optical reflection characteristic information of the object for acquiring information relating to the shape characteristics of the object in a direction of an optical axis toward the object that is perpendicular to the direction of scanning by the optical deflector.

10. The three-dimensional shape measurement apparatus according to claim 9 wherein the optical deflector is an acousto-optical deflector.

11. The three-dimensional shape measurement apparatus according to claim 9 wherein one of the two detection slits is located to the front of the said conjugate position and the other is located to the rear thereof.

12. The three-dimensional shape measurement apparatus according to claim 9 wherein he signal processing means includes a divider circuit and a function generator circuit.

13. The three-dimensional shape measurement apparatus according to claim 9 wherein a second optical deflector that is different from said optical deflector is provided for scanning perpendicular to the laser beam scanning direction of the said optical deflector at a frequency that is lower than the scanning frequency of the said optical deflector.

14. The three-dimensional shape measurement apparatus according to claim 13 wherein the second optical deflector is also used for scanning light reflected from the object, and at the detection slit the scanning is fixed in a direction that is perpendicular to the slit.

15. The three-dimensional shape measurement apparatus according to claim 13 wherein the second optical deflector is an oscillating mirror.

16. A three-dimensional shape measurement apparatus which directs a laser beam at an object, detects the light reflected back from the object, photoelectrically converts the light and subjects it to signal processing to obtain three-dimensional information about the object, comprising:
- a laser light source that generates a laser beam;
- an optical system for projecting the laser beam from the laser light source at the object;
- two detection apertures mutually displaced by a prescribed distance in the vicinity of a position that is optically conjugate with the object;
- two photosensors for detecting light reflected from the object passing through the respective detection apertures;
- a divider circuit for dividing the output of one photosensor by that of the other; and
- a correction means for correcting prescribed nonlinearity in the output of the divider.

17. The three-dimensional shape measurement apparatus according to claim 16 wherein the two detection apertures are detection slits.

18. The three-dimensional shape measurement apparatus according to claim 16 wherein, facing the object, one of the two detection slits is located to the front of the said conjugate position and the other is located to the rear thereof.

19. The three-dimensional shape measurement apparatus according to claim 16 wherein the correction means is a function generator.

20. The three-dimensional shape measurement apparatus according to claim 16 wherein the optical system includes first and second optical deflectors to scan the laser beam two-dimensionally.

21. The three-dimensional shape measurement apparatus according to claim 20 wherein the first optical deflector is an acousto-optical deflector.

22. The three-dimensional shape measurement apparatus according to claim 20 wherein the second optical deflector is an oscillating mirror.

23. The three-dimensional shape measurement apparatus according to claim 20 wherein the second optical deflector scans light reflected from the object and is also utilized for guiding the light to fix the scanning.

24. The three-dimensional shape measurement apparatus according to claim 20 wherein the scanning directions of the first and second optical deflectors are perpendicular to each other and the scanning frequency of the second optical deflector is lower than the scanning frequency of the first optical deflector.

25. A three-dimensional shape measurement apparatus which directs a laser beam at an eye fundus, detects light reflected back from the eye fundus, photoelectrically converts the light and subjects it to signal processing to obtain three-dimensional information about the eye fundus, comprising:
- a laser light source that generates a laser beam;
- a first optical deflector for scanning the laser beam in one direction at a predetermined frequency;
- a second optical deflector for scanning the laser beam in a direction that is perpendicular to the above said direction at a predetermined frequency;
- an optical system for projecting the laser beam scanned two-dimensionally by the first and second optical deflectors at the eye fundus;
- optical means for scanning light reflected from the eye fundus and guiding it so that scanning is stationary at least with respect to the direction of scanning by the second optical deflector;
- detection means for acquiring information relating to the shape characteristics of the eye fundus in a direction of an optical axis that is perpendicular to the direction of the scanning by the first and second optical deflectors, depending on displacement of the focal point of the light reflected from the eye fundus; and
- signal processing means for removing from the output signal of the detection means the influence of the optical reflection characteristics of the eye fundus.

26. The three-dimensional shape measurement apparatus for the eye fundus according to claim 25 wherein the first optical deflector is an acousto-optical deflector.

27. The three-dimensional shape measurement apparatus for the eye fundus according to claim 25 wherein the second optical deflector is an oscillating mirror.

28. The three-dimensional shape measurement apparatus for the eye fundus according to claim 25 wherein the optical means includes the second optical deflector.

29. The three-dimensional shape measurement apparatus for the eye fundus according to claim 25 wherein the scanning frequency of the second optical deflector is lower than the scanning frequency of the first optical deflector.

30. The three-dimensional shape measurement apparatus for the eye fundus according to claim 25 wherein the detection means includes two detection slits oriented in a direction parallel to the direction in which light reflected from the eye fundus is scanned and facing the eye fundus along an optical axis that is perpendicular to the direction of the scanning by the optical deflector, said detection slits being mutually displaced by a prescribed distance in the vicinity of a position that is optically conjugate with the eye fundus.

31. The three-dimensional shape measurement apparatus for the eye fundus according to claim 30 wherein one of the two detection slits is located to the front of the said conjugate position and the other is located to the rear thereof.

32. The three-dimensional shape measurement apparatus for the eye fundus according to claim 25 wherein the signal processing means includes a divider circuit and a function generator circuit.

* * * * *